US005641520A

United States Patent [19]

Howarth et al.

[11] Patent Number: 5,641,520
[45] Date of Patent: Jun. 24, 1997

[54] HALOGEN COMPOSITIONS FOR WATER TREATMENT

[75] Inventors: Jonathan N. Howarth, Atlanta, Ga.; Enrico J. Termine, West Lafayette, Ind.; Alan M. Yeoman, Duluth, Ga.

[73] Assignee: Great Lakes Chemical Corporation, West Lafayette, Ind.

[21] Appl. No.: 486,136

[22] Filed: Jun. 7, 1995

[51] Int. Cl.$^6$ .......................... A01N 59/00; A01N 43/50
[52] U.S. Cl. .................... 424/723; 424/661; 424/665; 514/389; 423/473
[58] Field of Search .......................... 424/723, 661, 424/665; 423/473; 514/389

[56] References Cited

U.S. PATENT DOCUMENTS

| | | | |
|---|---|---|---|
| 5,141,652 | 8/1992 | Moore, Jr. et al. | 210/754 |
| 5,338,461 | 8/1994 | Jones | 210/755 |
| 5,464,636 | 11/1995 | Hight et al. | 424/661 |
| 5,476,670 | 12/1995 | Hight et al. | 424/661 |
| 5,527,547 | 6/1996 | Hight et al. | 424/661 |

*Primary Examiner*—John Pak
*Attorney, Agent, or Firm*—Woodard, Emhardt, Naughton, Moriarty & McNett

[57] ABSTRACT

A method for providing aqueous solutions of HOBr or HOCl which includes adding bleach (NaOCl) to a solution of HBr or HCl an identified absorbance or color change in the resulting solution is detected. Dialkylhydantoins are optionally added to the resulting solution to suppress the formation of halate ions. The method provides a simple and reliable method for producing accurately defined solutions of hypohalous acids, which are useful in a variety of ways, including for disinfecting, cleaning, and odor control purposes.

8 Claims, 1 Drawing Sheet

HALOGEN COMPOSITIONS FOR WATER TREATMENT

BACKGROUND OF THE INVENTION

Halogenated 5,5-dialkylhydantoins (DAH) are common oxidizing biocides used for water sanitization. Examples of halogenated 5,5-alkylhydantoins include: dichlorodimethylhydantoin (DCDMH), dibromodimethylhydantoin (DBDMH), bromochlorodimethylhydantoin (BCDMH) and bromochloromethylethylhydantoin (BCMEH). The dialkylhydantoins are supplied in solid forms such as tablets or granules and are delivered to the system by water flow through a chemical erosion feeder charged with material. A combination of factors hamper the utility of this method. The rate of slug dosing is low because halogenated hydantoins are sparingly soluble in water (0.15–0.21%). The tablets and granules are often supplied as mixtures of chlorinated and brominated material since pure compounds are often difficult to produce. The different solubilities of the different compounds make accurate and reproducible delivery of oxidant difficult to attain. Also with different flow rates, the pressure drop across the chemical feeder varies, and this can produce non-uniform dissolution of the material. This also makes accurate and reproducible delivery difficult to attain.

Hypohalous acids (e.g., HOCl, HOBr) are also well known as oxidizing biocides for water treatment, and generally are generated in the liquid phase. Thus users avoid some of the limitations associated with solid chemicals. However, hypochlorous acid is unstable. Therefore, it is usually formed in-situ by treatment of the water with a precursor such as gaseous chlorine or sodium hypochlorite (bleach). Hypobromous acid is also unstable, and is formed in-situ by a number of methods. One method is the introduction of aqueous NaBr to the water, followed by activation with gaseous chlorine or bleach. Alternatively, stable perbromide ($Br_3^-$) solutions containing 30–40% $Br_2$ are added to the water. When injected into the water system, the $Br_3^-$ ion releases $Br^-$ ion and $Br_2$. The latter immediately hydrolyses to HOBr and HBr according to the equation:

$$Br_3^- = Br^- + Br_2 = HBr + HOBr$$

In another method, bromine chloride is introduced which hydrolyses in the water to hypobromous and hydrochloric acids in accordance with the following equation:

$$BrCl + H_2O = HOBr + HCl$$

All the foregoing methods of generating and delivering hypohalous acids suffer a number of drawbacks. Gaseous chlorine, bromine chloride, and perbromide solutions possess high halogen vapor pressures. These pose serious storage and handling hazards, and are highly corrosive to metering and delivery equipment. In the water system, chlorine, bromine chloride and perbromide solutions release one mole of strong acid (HCl or HBr) per mole of hypohalous acid. Low local pH conditions are corrosive to metals. For perbromide solutions, only one of the three Br moieties of the $Br_3^-$ ion materializes as HOBr, the other two are wasted. Sodium hypochlorite (bleach) is also unstable, and considerable amounts of NaOH are added to suppress deterioration. Therefore, application of bleach inadvertently increases the pH of the water and this can lead to local precipitation of metal hydroxides. The in-situ method of hypobromous acid generation by activation of NaBr with bleach or chlorine occurs under conditions of high dilution, and optimum control of the reaction stoichiometry is difficult. Underdosing of chlorine or bleach results in unreacted NaBr, while overdosing is a waste of material and can result in discharge limits being exceeded. In addition, for certain waters which are rich in ammonia and organic amines, the chlorine or bleach preferentially reacts to form stable chloramines which are unable to react with NaBr to form HOBr. Thus, NaBr is wasted.

Several of these limitations are addressed by an ex-situ system in which accurately defined, higher concentrations of hypobromous acid are prepared and stored for subsequent delivery to the water system. In this method, aqueous NaBr, bleach and HCl are metered to a reaction tank to produce a solution containing 2500 ppm HOBr. The hydrochloric acid neutralizes the hydroxide ions introduced with the bleach. The pH is maintained at 2.5–3.0, since incomplete conversion of $Br^-$ ion to HOBr is claimed under neutral conditions. The weaknesses of this method include the following. Bleach is unstable and must be analyzed routinely. Adjustments to the metering equipment are required to compensate for the varying bleach quality. The metering and control equipment is expensive. The process uses three components: aqueous NaBr, bleach, and HCl.

In a related issue, hypohalite ions are known to disproportionate under alkaline conditions to produce halate ions:

$$3XO^- = 2X^- + XO_3^-$$

Thus, chlorate can be formed during the manufacture and storage of bleach (to which NaOH is deliberately added to supress deterioration). Bromate can be formed under conditions of high local pH during the activation of NaBr by bleach. Both bromate and chlorate may be present in alkaline water to which the corresponding hypohalous acid (or precursor) has been introduced. Halate ions are undesirable byproducts. They are not biocidally active and are a waste of hypohalous acid. Also, they are contaminants under consideration for regulation by the EPA.

SUMMARY OF THE INVENTION

In one aspect of the present invention, there is provided a method for providing an aqueous solution of HOX, in which X is selected from bromine and chlorine, the method comprising the steps of providing an aqueous solution of HX, in which X is selected from the group consisting of bromine and chlorine, adding bleach to the HX solution while monitoring either the color or the absorbance at about 400 nm of the resulting solution, and discontinuing addition of bleach upon detection of a change (by colorimetry or visually) in color from orange to yellow. In certain embodiments, a dialkylhydantoin is added to the resulting solution to suppress the formation of bromate and/or chlorate ions.

It is an object of the present invention to provide a simple and reliable method for producing accurately defined solutions of HOBr and HOCl. These solutions contain up to five times more oxidizing halogen than those prepared from saturated solutions of solid halogenated hydantoins.

A further object of the present invention is to provide for the preparation of aqueous solutions containing hypohalous acids, but without production of halate ions.

Further objects and advantages of the present invention will be apparent from the description which follows.

DESCRIPTION OF THE PREFERRED EMBODIMENT

Figure 1:
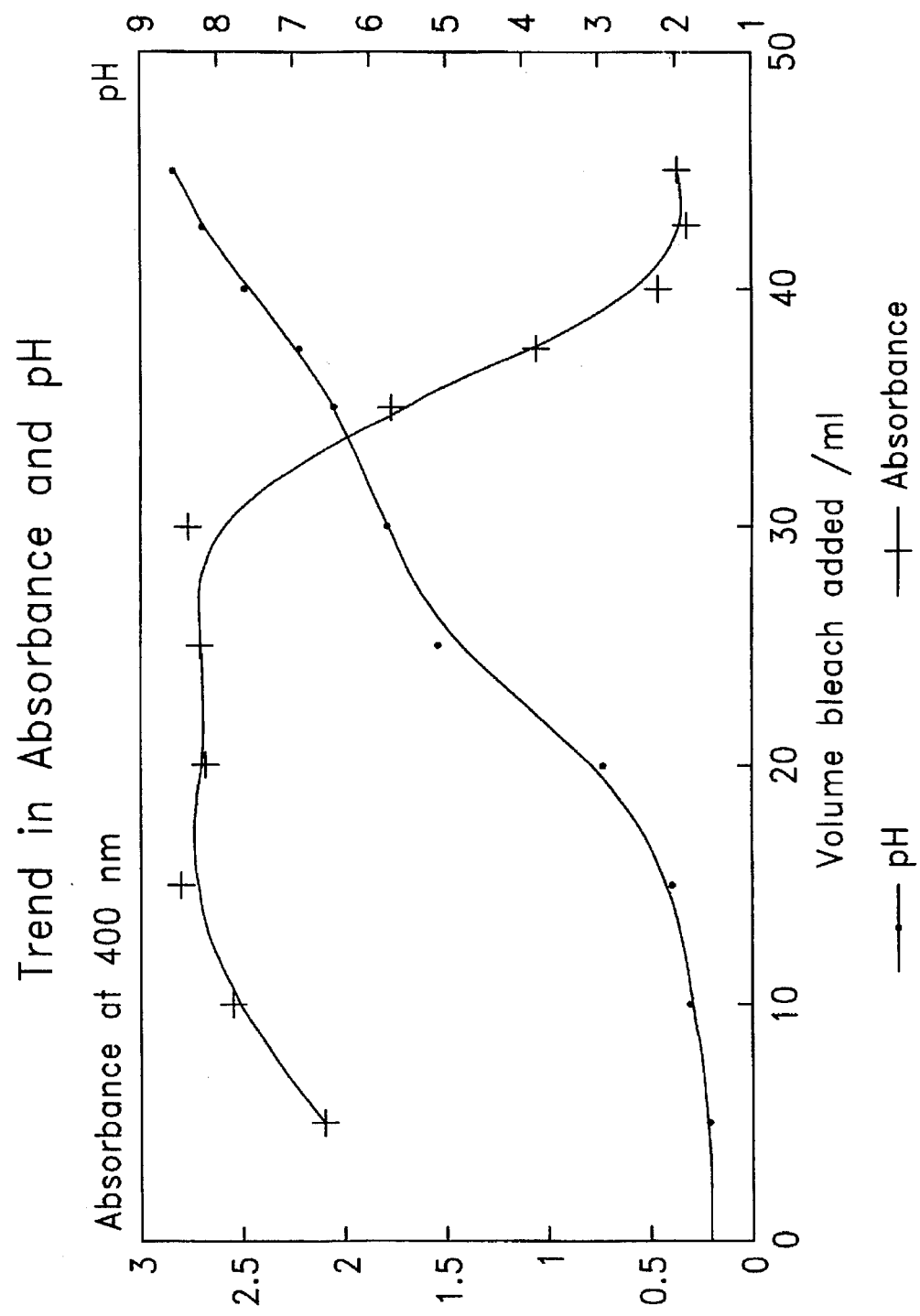
FIG. 1 is a graph showing the relationship between absorbance and pH in comparison to the volume of bleach added to an aqueous solution containing HBr.

For the purposes of promoting arm understanding of the principles of the invention, reference will now be made to the embodiment illustrated and specific language will be used to describe the same. It will nevertheless be understood that no limitation of the scope of the invention is thereby intended, such alterations, modifications, and further applications of the principles of the invention being contemplated as would normally occur to one skilled in the art to which the invention relates.

The present invention involves the use of HBr, optionally with DMH, which is activated with bleach. The system offers the user the advantages of a liquid product, and employs a built-in method for preparing accurately defined solutions with high levels of HOBr or N-bromo-DMH. Dosing is determined by the amount of HBr used, and is independent of the source, age, or concentration of the bleach. The dual combination of HBr and DMH offers a particular advantage in that the co-production of $BrO_3^-$ (a contaminant under consideration for regulation by the EPA) is suppressed to below detectable limits. The compositions of the present invention are useful for disinfecting and cleaning purposes, and in odor control applications.

In the practice of the present invention, HBr (or a dilution thereof) is added into a vessel containing water. Any source, age or concentration of bleach is added thereto (preferably with gentle agitation) until a change in absorbance or color (from dark orange to faint yellow) of the solution is detected. If the requirement is for free HOBr, this is delivered to the water straight away. If the requirement is for N-bromo-DMH, the appropriate amount of (preferably 10%) aqueous DMH solution is added. This can be delivered to the water, as-is, or stored for up to 5 days, and used as required.

The invention utilizes the discovery that absorbance or color changes can be used to produce a disinfecting solution of known composition from HBr and bleach (NaOCl). FIG. 1 shows the relationship between absorbance (at 400 nm) versus pH, when bleach is added to HBr in water. It can be seen that the absorbance initially increases and reaches a plateau. There then follows a sharp decrease in absorbance whereupon further amounts of bleach produce negligible changes. It can also be seen that as bleach is added, the pH of the solution increases from an initial value of 1.5, and reaches 7.5 when the absorbance of the solution is invariant. Analysis of the resulting solution showed that 98.4% of the $Br^-$ ion introduced as HBr was converted to HOBr.

It is also a feature of the invention that the sharp decrease in absorbance which signals almost quantitative conversion of $Br^-$ ion does not demand the use of a colorimeter. It can be detected visually, and is characterized by a sharp transition from dark orange to faint yellow. The dual combination of HBr and bleach provides the key to this easy method of $Br^-$ ion activation; the NaOCl of the bleach oxidizes the $Br^-$ ion, while the NaOH of the bleach neutralizes the $H^+$ ion. The pH swing is a vital feature of the color change. At low pH, the predominant species is elemental $Br_2$ ($\lambda$max 390 nm), hence the orange color. As more bleach is added, the pH increases, $Br_2$ hydrolyses to HOBr and releases HBr which under the ensuing pH conditions can only be oxidized to more HOBr. Thus, the dark orange to faint yellow transition signals the depletion of $Br_2$ and almost quantitative conversion of the HBr to HOBr.

Activation of HBr by bleach with colorimetric or visual determination of the end-point has been found to operate with any source of bleach, regardless of its age or NaOCl concentration. We have discovered that the NaOCl:NaOH mole ratio unexpectedly does not vary with age or with concentration. Therefore, weaker or aged bleach simply requires the use of larger quantities of bleach than when strong or fresh material is used. Consequently, bromine oxidant levels are based solely on the amount of HBr introduced to the solution. Since this is easy to measure accurately, and since HBr is indefinitely stable, the system offers a simple and convenient method of preparing solutions of well-defined composition, and the need for traditional analysis of the bleach is eliminated. As the data in Table 1 evidences, high concentrations of accurately defined HOBr or N-bromo-DAH levels can be prepared. The high dilution problems of underdosing or overdosing chlorine or bleach which are associated with in-situ methods of NaBr activation are avoided. Furthermore, the ex-situ nature of the process means that chlorine or bleach is not lost to rapid chloramine formation, but is manifest as HOBr.

By comparison with the data in Table II, it can be seen that by controlling the mole ratio of DAH:HOX, halogenated 5,5-dialkylhydantoins can be prepared directly in the liquid phase. With a mole ratio in excess of 1.16:1, the products remain in solution at all but the highest concentrations of HOX. Lower mole ratios ((1:1) result in precipitation of material and the advantages of an "all-liquid" product are lost. Using the method described, halogenated dialkylhydantoins can be prepared at concentrations 2–3 times higher than saturated solutions of solid chemicals. Slug dosing is correspondingly more rapid, the pre-dissolution step is eliminated, and storage tanks are conveniently smaller.

The resulting solutions of the present invention have desirable characteristics. The solutions have a neutral pH (6–8), high concentration (0.03–0.1M) of oxidant, negligible halogen vapor pressures, and close to quantitative conversion of $X^-$ ions to HOX. The solutions are generated outside the water system, and can be conveniently delivered to the water system. This represents a considerable improvement over other hypohalous acid precursors ($Cl_2$, BrCl, $Br_3^-$ solutions) which have dangerously high vapor pressures and release strong acid when introduced to the water. Furthermore, a neutral pH has less impact on the treated water than systems employing highly basic solutions of bleach.

Contrary to methods of $Br^-$ ion activation which demand acidic buffering (because incomplete conversion to HOBr or $Br_2$ is claimed), the dual combination of HBr and bleach allows the pH to swing and results in rapid conversion of $Br^-$ ion across a pH range of about 0.7 to about 7.5. Unlike methods which are designed to produce elemental $Br_2$ or involve the use of $Br_3^-$ solution, almost all the Br moieties materialize as HOBr.

Hypobromite anions are known to disproportionate under alkaline conditions to bromate anions:

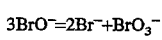

$$3BrO^-=2Br^-+BrO_3^-$$

This, bromate can be formed in water systems operating at high bulk pH (such as cooling towers), and under conditions of high local pH (such as in the traditional activation of NaBr by bleach). However, oxidation-reduction-potential measurements in the presence of dialkylhydantoins such as DMH, indicate that $OBr^-$ ions are not free entities, but are strongly associated to the DAH molecules. Consequently, the undesirable disproportionation of free $OBr^-$ ions to $BrO_3^-$ ions is suppressed by the presence of dialkylhydantoins. Dialkylhydantoins are useful in which each alkyl group is independently selected from groups having 1 to 4 carbons, with dimethylhydantoin being preferred. Dialkylhydantoins may be added as such, or as a result of breakdown or reaction of other components, and includes the addition of compounds such as halogenated compounds (e.g., bromochlorodimethylhydantoin). The solutions thus prepared are characterized as follows: colorless, close to neutral pH (6–8), high concentration (0.03–0.075M) of oxidant, negligible halogen vapor pressures, devoid of precipitated material (by controlling DAH:HOX mole ratio around 1:1), low to undetectable levels of Halate ions, close to quantitative conversion of $X^-$ ions to HOX, and are gnerated outside the water system.

EXAMPLE 1

Hydrobromic acid solution (48%) (3.45 ml) was added to water. (900 ml) to give a solution of pH 1.5. Aliquots of household bleach (4.99% NaOCl) were added with gentle stirring. After each addition, the absorbance at 400 nm and the pH of the solution were measured. FIG. 1 shows a plot of the absorbance and pH as a function of bleach added. The absorbance initially increased and reached a plateau. There then followed a sharp decrease in absorbance whereupon addition of further amounts of bleach produced negligible changes in the absorbance. It can also be seen that as the bleach was added, the pH of the solution increased from the initial value of 1.5 and reached 7.5 when the absorbance of the solution was invariant.

The resulting solution was made tip to 1000 ml in a volumetric flask and analyzed using iodometric titration. A 1000-fold dilution of this was subjected to DPD-FAS analysis, in the presence and absence of glycine. The results showed that 98.4% of the $Br^-$ ion introduced as HBr was converted to HOBr. The concentration of HOBr in solution was 0.0301M, corresponding to 2916 ppm.

EXAMPLE 2

Hydrobromic acid solution (48%) (3.45 ml) was added to water (900 ml) to give a solution of pH 1.5. Household bleach (4.85% NaOCl) was added with gentle stirring until the solution turned from bright orange to a faint yellow color. The amount of bleach added was 46.24 g. The pH of the resulting solution was 7.0. After making the solution up to 1000 ml, analysis revealed that the HOBr concentration was 0.0307M, corresponding to 2974 ppm.

EXAMPLE 3

Hydrobromic acid solution (48%) (3.45 ml) was added to water (900 ml) to give a solution of pH 1.5. Seventeen-month old household bleach (3.71% NaOCl) was added with gentle stirring until the solution turned from bright orange to a faint yellow color. The actual amount of bleach added was 66.1 g. The pH of the resulting solution was 6.9, and after making up to 1000 ml, analysis revealed the HOBr concentration as 0.0306M, corresponding to 2965 ppm.

EXAMPLE 4

Hydrobromic acid solution (48%) (3.45 ml) was added to water. (900 ml) to give a solution of pH 1.6. Industrial grade bleach (13.3% NaOCl) was added with gentle stirring until the solution turned from bright orange to faint yellow. The amount of bleach added was 21.79 g. The pH of the resulting solution was 6.7. After making up to 1000 ml, analysis revealed a HOBr concentration of 0.0315M HOBr, corresponding to 3052 ppm.

EXAMPLE 5

Hydrobromic acid solution (48%) (3.45 ml) was added to water (900 ml) to give a solution of pH 1.7. Industrial grade bleach (13.3% NaOCl) was added with gentle stirring until the solution turned from bright orange to faint yellow. The amount of bleach added was 21.24 g. The pH of the resulting solution was 6.5. After making up to 1000 ml, analysis revealed the HOBr concentration as 0.0369M, corresponding to 3575 ppm.

Dimethylhydantoin (3.92 g, 0.0306 moles dissolved in 40 ml of water) was added to the solution (mole ratio DMH:HOBr=0.83). The faint yellow color was discharged and the solution became completely colorless. However, shortly thereafter, a white precipitate began to develop. After two hours, the precipitate was filtered from the solution. The supernatant solution was re-analyzed, and found to have lost 35% of its oxidizing material. The precipitate was oven-dried at 50° C. overnight. High-field NMR spectroscopy identified the material as 1,3-dibromo-5,5-dimethylhydantoin.

EXAMPLE 6

Hydrobromic acid solution (48%) (3.45 ml) was added to water (900 ml) to give a solution of pH 1.7. Industrial grade bleach (13.3% NaOCl) was added with gentle stirring until the solution turned from bright orange to faint yellow. The amount of bleach added was 17.67 g. The pH of the resulting solution was 6.4 and after making up to 1000 ml, analysis revealed a HOBr concentration of 0.0318M HOBr, corresponding to 3081 ppm. Dimethylhydantoin (4.72 g, 0.0368 moles dissolved in 40 ml of water) was added to the solution (mole ratio DMH:HOBr=1.16). The faint yellow color was discharged and the solution became completely colorless. No precipitation was evident. On standing for two days, a very slight amount of precipitate was noticed. The supernatant solution was re-analyzed and found to have lost only 7.5% of its oxidizing material.

EXAMPLE 7

Hydrobromic acid solution (48%) (5.62 ml) was added to water (850 ml) to give a solution of pH 1.0. Aged industrial grade bleach (8.23% NaOCl) was added with gentle stirring until the solution turned from bright orange to faint yellow. The amount of bleach added was 43.66 g. The pH of the resulting solution was 7.4 and after making up to 1000 ml, analysis revealed a HOBr concentration of 0.051M HOBr, corresponding to 4941 ppm. Dimethylhydantoin (6.66 g, 0.052 moles dissolved in 50 ml of water) was added to the solution (mole ratio DMH:HOBr=1.02). The faint yellow color was discharged and the solution became completely colorless. However, a white precipitate developed within a few seconds.

EXAMPLE 8

Hydrobromic acid solution (48%) (5.62 ml) was added to water (850 ml) to give a solution of pH 1.1. Aged industrial grade bleach (8.23% NaOCl) was added with gentle stirring until the solution turned from bright orange to faint yellow. The amount of bleach added was 42.73 g. The pH of the resulting solution was 7.2 and after making up to 1000 ml, analysis revealed a HOBr concentration of 0.0497M HOBr, corresponding to 4815 ppm. Dimethylhydantoin (9.62 g, 0.075 moles dissolved in 100 ml of water) was added to the solution (mole ratio DMH:HOBr=1.51). The faint yellow color was discharged and the solution became completely colorless. No precipitate was evident on standing for 5 days.

EXAMPLE 9

Hydrobromic acid solution (48%) (11.25 ml) was added to water (700 ml) to give a solution of pH 0.7. Aged industrial grade bleach (8.23% NaOCl) was added with gentle stirring until the solution turned from bright orange to faint yellow. The amount of bleach added was 99.88 g. The pH of the resulting solution was 7.2 and after making up to 1000 ml, analysis revealed a HOBr concentration of 0.1009M HOBr, corresponding to 9777 ppm.

EXAMPLE 10

Hydrobromic acid solution (48%) (11.25 ml) was added to water (700 ml) to give a solution of pH 0.7. Aged industrial grade bleach (8.23% NaOCl) was added with gentle stirring until the solution turned from bright orange to faint yellow. The amount of bleach added was 96.27 g. The pH of the resulting solution was 7.4 and after making up to 1000 mL, analysis revealed a HOBr concentration of 0.1004M HOBr, corresponding to 9728 ppm. Dimethylhydantion (25.6 g, 0.2 moles dissolved on 200 ml of water) was added to the solution (mole ratio DMH:HOBr=1.99). The faint yellow color was discharged and the solution became completely colorless. However, within a few minutes, a white precipitate developed.

Table I summarizes the above data, along with a measure of the amount of oxidant in the resulting solutions, expressed in mg/L as $Cl_2$.

end-point determination was used. In other cases, predetermined amounts of bleach were weighed and introduced. The solutions were either buffered at a given pH by co-addition of 1M HCl, or were not buffered, and the pH was allowed to vary as the bleach was introduced. Dimethylhydantoin was added to some of the samples, introduced before or after bleach activation.

The oxidant level of each solution was measured, and within an hour, the solutions were subject to ion-chromatography for determination of $BrO_3^-$ ion.

Table III summarizes the activation conditions, and the results obtained.

TABLE I

| Example | Volume 48% HBr/ml | Bleach Strength/ % NaOCl (Amount added/g) | Initial pH Final pH | End-point detection method | [HOBr]/M | Mole Ratio DMH: HOBr | Precip. | Amount of oxidant (mg/L as $Cl_2$) |
|---|---|---|---|---|---|---|---|---|
| 1 | 3.45 | 4.99 (47.5 ml) | 1.5 7.5 | colorimetry | 0.0301 | — | — | 2137 |
| 2 | 3.45 | 4.85 (46.24) | 1.5 7.0 | visual | 0.0307 | — | — | 2179 |
| 3 | 3.45 | 3.71 (66.1) | 1.5 6.9 | visual | 0.0306 | — | — | 2172 |
| 4 | 3.45 | 13.3 (21.79) | 1.6 6.7 | visual | 0.0315 | — | — | 2236 |
| 5 | 3.45 | 13.3 (21.24 | 1.7 6.5 | visual | 0.0369 | 0.83 | yes | 2619 |
| 6 | 3.45 | 13.3 (17.67) | 1.7 6.4 | visual | 0.0318 | 1.16 | no | 2257 |
| 7 | 5.62 | 8.23 (43.66) | 1.0 7.4 | visual | 0.0510 | 1.02 | yes | 3621 |
| 8 | 5.62 | 8.23 (42.73) | 1.1 7.2 | visual | 0.0497 | 1.51 | no | 3528 |
| 9 | 11.25 | 8.23 (99.88) | 0.7 7.2 | visual | 0.1009 | — | — | 7163 |
| 10 | 11.25 | 8.23 (96.27) | 0.7 7.4 | visual | 0.1003 | 1.99 | yes | 7121 |

TABLE II

Water solubility of solid halogenated hydantoins, and the amount of halogen dissolved in a saturated solution of the material.

| Material | Solubility/% | Saturated Solution mg/L as $Cl_2$ |
|---|---|---|
| Dichlorodimethylhydantoin | 0.21 | 1513 |
| Dibromodimethylhydantion | 0.11 | 542 |
| Bromo-chlorodimethylhydantoin | 0.15 | 825 |

In a subsequent series of experiments, 48% HBr or 45.59% NaBr was activated with bleach (4.85% NaOCl). In some cases, the visual dark orange-faint yellow) method of

TABLE III

| Example | Br⁻ ion source | pH | Bleach added/g | End-point detection | DMH | [Oxidant]/ M | BrO$_3^-$/ mg/L |
|---|---|---|---|---|---|---|---|
| 1 | 45.6% NaBr (6.841 g) | buffered at pH 2.5 with 1M HCl | 46.597 | — | no | 0.0296 | <10 |
| 2 | 45.6% NaBr (6.829 g) | buffered at pH 7.0 with 1M HCl | 46.827 | — | no | 0.0309 | 126 |
| 3 | 45.6% NaBr (6.829 g) | buffered at pH 7.0 with 1M HCl | 46.452 | — | yes 3.929 g | 0.0309 | <10 |
| 4 | 48% HBr (3.45 ml) | Initial 1.5 Final 7.0 | 46.240 | visual | no >3.915 g | 0.0307 | 70 |
| 5 | 48% HBr (3.45 ml) | Initial 1.5 Final 6.7 | 47.211 | visual | yes | 0.0362 | <10 |
| 6 | 45.6% NaBr (6.878 g) | Initial 5.9 Final 8.8 | 46.840 | — | yes 4.743 g | 0.0313 | <10 |

The data in Table III clearly show that DMH is effective in suppressing BrO$_3^-$ ion formation, especially under bulk alkaline conditions, or local alkaline conditions which develop on introduction of bleach. It can also be seen that under conditions of high acidity (Example 1) BrO$_3^-$ ion formation does hot occur.

The present invention is also useful for providing solutions of HOCl. Substitution of HCl for HBr, as in the foregoing examples, yields suitable solutions of HCl upon combination with the bleach.

The methods and compositions of the present invention are advantageously employed for the treatment of various aqueous systems, including cooling water, recreational water, municipal wastewater, pulp and paper whitewater, process waters and irrigation water.

What is claimed is:

1. A composition prepared by the process comprising the steps of:
   a. providing an aqueous solution of HBr;
   b. adding NaOCl to the HBr solution while monitoring the color of the resulting solution;
   c. discontinuing addition of NaOCl upon detection of a change in color from orange to yellow; and
   d. adding sufficient amount of a non-halogenated 5,5-dialkylhydantoin compound to the resulting solution to suppress the formation of BrO$_3^-$, the non-halogenated 5,5-dialkylhydantoin compound having alkyl groups having 1 to 4 carbons.

2. The composition of claim 1 in which step d. comprises adding non-halogenated dialkylhydantoin in a mole ratio to HOBr of greater than 1:1.

3. The composition of claim 1 in which step d. comprises adding a non-halogenated 5,5-dialkylhydantoin having alkyl groups selected from the group consisting of methyl and ethyl.

4. The composition of claim 3 in which step d. comprises adding non-halogenated 5,5-dimethylhydantoin.

5. A composition prepared by the process comprising the steps of:
   a. providing an aqueous solution of HBr;
   b. adding NaOCl to the HBr solution while monitoring the absorbance at about 400 nm of the resulting solution;
   c. discontinuing addition of NaOCl upon detection of an about 5 to about 10 fold decrease in absorbance as measured at about 400 nm; and
   d. adding sufficient amount of a non-halogenated 5,5-dialkylhydantoin compound to the resulting solution to suppress the formation of BrO$_3^-$, the non-halogenated 5,5-dialkylhydantoin compound having alkyl groups having 1 to 4 carbons.

6. The composition of claim 5 in which step d. comprises adding non-halogenated dialkylhydantoin in a mole ratio to HOBr of greater than 1:1.

7. The composition of claim 5 in which step d. comprises adding a non-halogenated 5,5-dialkylhydantoin having alkyl groups selected from the group consisting of methyl and ethyl.

8. The composition of claim 7 in which step d. comprises adding non-halogenated 5,5-dimethylhydantoin.

* * * * *

UNITED STATES PATENT AND TRADEMARK OFFICE
CERTIFICATE OF CORRECTION

PATENT NO. : 5,641,520
DATED : June 24, 1997
INVENTOR(S) : Jonathan N. Howarth et al.

It is certified that error appears in the above-identified patent and that said Letters Patent is hereby corrected as shown below:

In col. 3, line 4, please change "arm" to --an--.

In col. 4, line 24, please change "(1:1" to --<1:1--

In col. 4, line 57, please change "This" to --Thus--.

In col. 5, line 28, please change "tip" to --up--.

Signed and Sealed this

Sixth Day of January, 1998

Attest:

BRUCE LEHMAN

Attesting Officer       Commissioner of Patents and Trademarks